United States Patent [19]
Barbieri et al.

[11] Patent Number: 5,069,341
[45] Date of Patent: Dec. 3, 1991

[54] DISPOSABLE SINGLE-USE DRIP-FEED DEVICE WITH A COVER FOR THE NEEDLE AFTER USE

[76] Inventors: Giuseppe Barbieri, Via Pieve del Pino, 38 Sasso Marconi (Bologna), Italy, 40037; Deanna Bordini, Via Grazia Deledda, 2 Montale di Castelnuovo Rangone (Modena); Luciano Gatti, Via Grazia Deledda, 4 Montale di Castelnuovo Rangone (Modena), both of Italy, 41051

[21] Appl. No.: 689,169

[22] Filed: Apr. 22, 1991

[30] Foreign Application Priority Data

May 29, 1990 [IT] Italy .................................. 3525 A/90

[51] Int. Cl.5 ............................................. B65D 85/24
[52] U.S. Cl. ...................................................... 206/365
[58] Field of Search ......................................... 206/365

[56] References Cited
U.S. PATENT DOCUMENTS 4,927,019 5/1990 Haber et al. ........................ 206/365
4,943,284 7/1990 Erlich ................................. 206/365

Primary Examiner—William I. Price
Attorney, Agent, or Firm—Darby & Darby

[57] ABSTRACT

This single-use drip-feed device comprises, in this order, mutually joined together and communicating, a connector which can be linked to a feed tube supplying a drip-feed liquid, a narrow linking tube and a needle having two diametrically opposite flexible tabs for handling, and with the aim of rendering harmless the needle after use, has a tubular cover fitted in a freely sliding manner over the narrow tube, with, beginning at the extremity towards the needle, two longitudinal slots diametrically opposite each other into which the tabs of the needle are inserted so as to cover completely the point of the latter; the cover is made of a material which cannot be pierced by the needle but at the same time is sufficiently elastic to permit insertion of the tabs into the slots.

4 Claims, 1 Drawing Sheet

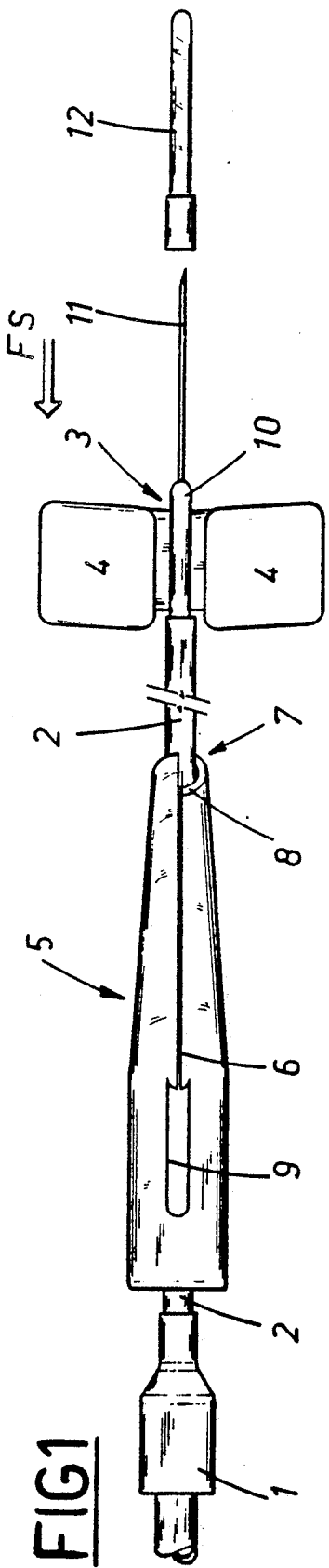
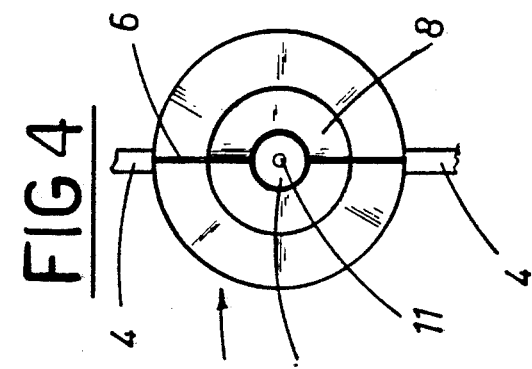
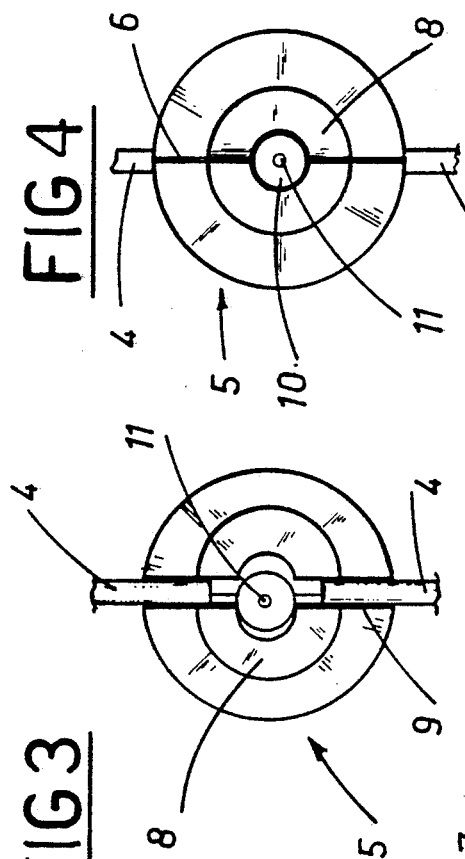
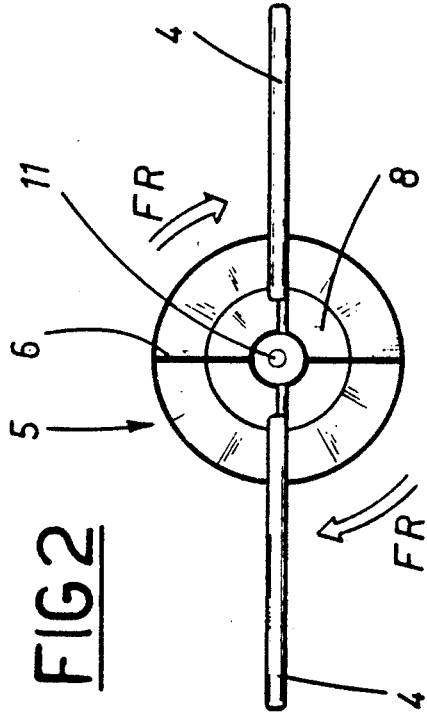
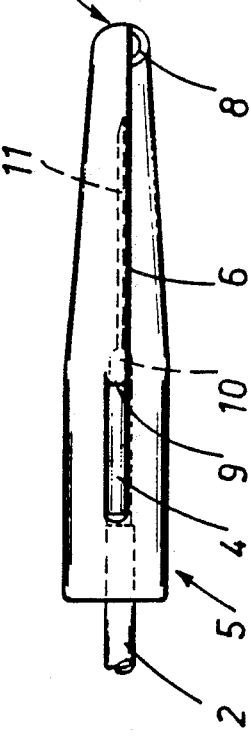

DISPOSABLE SINGLE-USE DRIP-FEED DEVICE WITH A COVER FOR THE NEEDLE AFTER USE

BACKGROUND of the INVENTION

This invention concerns a disposable single-use drip-feed device with a cover for the needle after use.

The continuous spread of infectious diseases has meant that all invasive instruments used in treating patients are designed in such a way as to be rendered completely harmless once used.

This is particularly important for medical personnel who can easily injure themselves with objects which at first sight seem harmless.

This is the case with drip-feed devices consisting of a connector which couples with a tube supplying drip-feed liquid and of a needle linked together by a narrow tube. For handling, the needle is provided with a pair of flexible tabs diametrically opposite each other.

Before the drip-feed device is used, the needle is sheathed in a cap which is flush with the structure which the tabs are attached to.

Since the needle and the structure to which it is attached are very small so as to enable the needle to be inserted into the vein while almost in contact with and parallel to the skin, this cap must also be very small.

Consequently the cap is often lost immediately after it is removed from the needle, and in any case, it is difficult to replace it on the needle without running the risk of pricking oneself.

Immediate disposal of the whole device in a suitable container after use easily overcomes the problem of the risk of injury, but sometimes may be difficult to do when it is necessary to perform a number of tasks almost simultaneously and there is no time available to think about one's personal safety, as when the life of a patient may depend upon swift action being taken.

This aspect is even more serious if, as mentioned above, the patient is suffering from an easily transmitted infectious disease. Obviously, in the case of a drip-feed device the risk would be great, since the needle would spread contagion through an injury and not by mere contact.

The aim of the present invention is to design the drip-feed mechanism in such a way that it may be swiftly and easily made harmless, thus eliminating the above mentioned drawbacks.

SUMMARY of the INVENTION

The stated aim is realized in a drip-feed device comprising at least a connector which can be linked to a feed tube supplying a drip-feed liquid, a narrow linking tube and a needle having two diametrically opposite flexible tabs for handling, all joined together and communicating.

With the aim of rendering harmless the needle after use, there is a tubular cover fitted in a freely sliding manner over the narrow tube, with, beginning at the extremity towards the needle, two longitudinal slots into which the tabs of the needle are inserted so as to cover completely the point of the latter; the cover is made of a material which cannot be pierced by the needle but at the same time is sufficiently elastic to permit insertion of the tabs into the slots.

The main advantage of the invention is that it is simple and extremely economical to manufacture and simple to use.

BRIEF DESCRIPTION of the DRAWINGS

The invention will now be described in detail, by way of example, with the aid of the accompanying drawings, in which:

FIG. 1 is a enlarged side view of the drip-feed device;

FIGS. 2, 3 and 4 are enlarged plan views of the needle and the cap of the device in FIG. 1 in three successive stages following use;

FIG. 5 is a side view in reduced scale of FIG. 4 in which the device is ready for completely safe disposal and is illustrated in a different form.

DESCRIPTION of the PREFERRED EMBODIMENTS

The drip-feed device according to the invention is of the type comprising a connector 1, linkable to a feed tube supplying a drip-feed liquid, and a needle 3, which are connected to each other by a narrow tube 2.

The connector 1, the narrow tube 2 and the needle 3 communicate and are irremovably joined together. The needle 3 consists of a tubular structure 10 rigidly connected to the narrow tube 2 and fixed to the actual needle 11.

Two flexible tabs 4 for manipulating the entire needle 3 extend in diametrically opposite directions from the structure 10.

The drip-feed device in question is completed by a cap 12 which is designed to fit over the needle 11 and which touches the structure 10.

According to the present invention, over the narrow tube 2 is fitted, in a freely sliding manner, a tubular cover 5 which has, on the extremity 7 towards the needle 3, a pair of longitudinal slots 6 into and along which the tabs 4 of the needle 3 can be inserted.

The cover 5 and the slots 6 are of such a length that when the tabs 4 have run the whole length of the slots 6 and approach the closed ends of the latter, the needle 3 is completely housed within the cover 5.

The cover 5 must be made from a material which is sufficiently hard to prevent the needle 11 from piercing it, yet at the same time, sufficiently elastic to permit easy insertion of the tabs 4 into the slots 6.

As can be seen in FIGS. 1 and 5, the two halves 8 of the extremity 7 of the cover 5 formed by the slots 6, are at an angle to the transversal plane of the cover itself. Practically the two halves 8 provide two guides for automatic insertion of the tabs 4 into the slots 6.

In FIG. 1 it can be seen that if the connector 1 is moved away from the cover 5, the needle 3 is moved nearer to the cover 5. The tabs 4 can come into contact with the two halves 8 in any position, and thanks to their slant and the flexibility of the narrow tube 2 slide along the same because of the traction exerted on the latter (see FIG. 1 arrow FS) and revolve around the axis of the needle 3 and of the cover 5 (see FIG. 2 Arrow FR) until they are perfectly aligned with the slots 6 (see FIG. 3). Subsequently the tabs 4 enter the slots 6 and move along them completely until the needle 11 is completely inside the cover 5 (see FIGS. 4 and 5). A further characteristic of the device according to the present invention is that the slots 6 are envisaged as forming, at their closed ends, a seat 9 which can house the tabs 4 in their entirety (see FIGS. 1 and 5).

Furthermore, the seats 9 are so shaped, where their extremities communicate with the slots 6, as to prevent the tabs 4 from leaving them A design which suits this purpose is shown in FIG. 5 where the seats 9 have rounded extremities and the slots 6 depart from them eccentrically with respect to the axis of the same seats 9 so as to divide these rounded extremities into two arcs of different width. In this way, any pressure on the tabs 4 with the intention of dislodging them from the seats 9 would make the same hit against only the wider arc. It must in fact be remembered that if the tabs 4 are completely lodged within the seats 9 and the cover 5 is elastic, the seats 9 allow the cover 5 to return to its initial position in which the two halves defined by the slots 6 are in mutual contact as shown in FIG. 5. If the slots 6 and the seats 9 were coaxial, as shown by the dotted line in FIG. 1, the tabs 4 could exert pressure on the two sides of each groove 6 and force them apart.

The drip-feed device described in the present invention fully reaches its aim, since after use it is sufficient to move the connector 1 and the cover 5 away from each other for the needle 11 to move completely inside the cover 5 thus preventing the needle 11 from protruding even slightly from the same cover.

The present invention has the advantage of being simple to manufacture and use, which makes it both extremely effective and easy and quick to use under all circumstances.

There is the further advantage that its cost is extremely low.

WHAT IS CLAIMED

1. Single-use drip-feed device with a cover for the needle after use, comprising, in this order, and communicating and irremovably joined together, a connector (1) linkable to a feed tube supplying a drip-feed liquid, a narrow tube (2) and a needle (3) having two diametrically opposite flexible tabs (4) for handling, wherein over the narrow tube (2) is fitted, in a freely sliding manner, a tubular cover (5) which has, at the extremity (7) towards the said needle (3), a pair of longitudinal slots (6) on opposite sides with respect to its longitudinal axis; the said slots (6) are of a length such that, when the said tabs (4) approach the closed ends of the said slots (6), the point of the needle (3) is completely contained within the said tubular cover (5); this being made of a material which is sufficiently hard to prevent the point of the needle (3) from piercing it, yet at the same time, sufficiently elastic to permit insertion of the said tabs (4) into the said slots (6).

2. Drip-feed device as in claim 1, wherein the two halves (8) into which the extremity (7) of the said tubular cover (5) towards the said needle (3) is divided by the grooves (6) are both at an angle to the transversal plane of the cover itself (5) thus forming two guides for the said tabs (4) for automatic insertion of the tabs (4) into the slots (6) when the said connector (1) is moved away from the said tubular cover (5) after use of the drip-feed device.

3. Drip-feed device as in claim 1, wherein the closed ends of the said slots furthest away from the said needle are shaped so as to form longitudinal seats (9) which completely house the said tabs (4).

4. Drip-feed device as in claim 3, wherein the said seats (9) are so shaped, at the ends contiguous with the said slots (6), as to prevent the said tabs (4) from escaping once they have been inserted in the same seats (9).

* * * * *